(12) United States Patent
Hellerbrand et al.

(10) Patent No.: US 9,526,761 B2
(45) Date of Patent: Dec. 27, 2016

(54) DRIED RECONSTITUTED VESICLE FORMATION FOR PHARMACEUTICAL APPLICATION

(75) Inventors: Klaus Hellerbrand, Moorenweis (DE); Andreas Schuetz, Stockdorf (DE); Rainer Sigl, Puchheim (DE)

(73) Assignee: SCIL Technology GmbH, Martinsried (DE)

( * ) Notice: Subject to any disclaimer, the term of this patent is extended or adjusted under 35 U.S.C. 154(b) by 1807 days.

(21) Appl. No.: 12/419,167

(22) Filed: Apr. 6, 2009

(65) Prior Publication Data
US 2009/0285880 A1 Nov. 19, 2009

(30) Foreign Application Priority Data

Oct. 6, 2006 (EP) ..................................... 06021093

(51) Int. Cl.
*A61K 9/127* (2006.01)
*A61K 9/19* (2006.01)
*A61K 38/18* (2006.01)
*A61K 9/00* (2006.01)

(52) U.S. Cl.
CPC ......... *A61K 38/1875* (2013.01); *A61K 9/0019* (2013.01); *A61K 9/0085* (2013.01); *A61K 9/1272* (2013.01); *A61K 9/127* (2013.01); *A61K 9/19* (2013.01)

(58) Field of Classification Search
USPC ......................................................... 424/450
See application file for complete search history.

(56) References Cited

U.S. PATENT DOCUMENTS

| | | | | |
|---|---|---|---|---|
| 4,229,360 A | * | 10/1980 | Schneider et al. ............. 264/4.6 |
| 4,247,411 A | * | 1/1981 | Vanlerberghe ........... A61K 8/14 264/4.6 |
| 4,897,353 A | | 1/1990 | Carpenter et al. |
| 5,034,228 A | * | 7/1991 | Meybeck et al. ............. 424/401 |
| 5,569,464 A | * | 10/1996 | Endo et al. ................... 424/450 |
| 5,709,879 A | * | 1/1998 | Barchfeld et al. ............ 424/450 |
| 6,066,331 A | * | 5/2000 | Barenholz et al. ........... 424/450 |
| 7,238,367 B2 | * | 7/2007 | Tardi et al. ................... 424/450 |
| 2005/0181037 A1 | * | 8/2005 | Ahmad et al. ................ 424/450 |
| 2006/0110441 A1 | * | 5/2006 | Wong et al. .................. 424/450 |
| 2011/0033505 A1 | * | 2/2011 | Charmot et al. .............. 424/400 |
| 2011/0071056 A1 | * | 3/2011 | Saini et al. ................... 507/119 |

FOREIGN PATENT DOCUMENTS

| | | |
|---|---|---|
| EP | 0211647 A1 | 2/1987 |
| WO | WO 92/02208 A1 | 2/1992 |
| WO | WO 95/09610 A1 | 4/1995 |
| WO | WO 97/10851 A3 | 3/1997 |

OTHER PUBLICATIONS

C. Kirby et al., "Dehydration-Rehydration Vesicles: A Simple Method for High Yield Drug Entrapment in Liposomes", Biotechnology, Butterworths, London, GB, vol. 2., No. 11, Nov. 1, 1984, pp. 979-984.

Suggy S. Chrai et al; Liposomes: A Review, Part I: Manufacturing Issues; Pharmaceutical Technology, Apr. 2002; 4 pages. This article previously was published in BioPharm, 14[11], Oct. 14, 2001.

F. Frezard et al; Liposomes: From Biophysics to the Design of Peptide Vaccines, Brazilian Journal of Medical and Biological Research [1999] 32; pp. 181-189;ISSN 0100-879X.

* cited by examiner

*Primary Examiner* — Gollamudi Kishore
(74) *Attorney, Agent, or Firm* — Arent Fox LLP

(57) ABSTRACT

The present invention relates to dried reconstituted vesicle (DRV) compositions and water based formulations thereof, which contain one or more therapeutic agents (e.g. hydrophilic protein). More particularly, it relates to DRVs comprising at least one lipid and a fusion promoting agent which after reconstitution form large multilamellar liposomes encapsulating an active agent in an aqueous phase.

7 Claims, 3 Drawing Sheets

```
                        SEQUENCE LISTING

<160> NUMBER OF SEQ ID NOS: 4

<210> SEQ ID NO 1
<211> LENGTH: 107
<212> TYPE: PRT
<213> ORGANISM: Homo sapiens

<400> SEQUENCE: 1

Gly Pro Met Pro Lys Leu Ala Asp Arg Lys Leu Cys Ala Asp Gln Glu
1               5                   10                  15

Cys Ser His Pro Ile Ser Met Ala Val Ala Leu Gln Asp Tyr Met Ala
            20                  25                  30

Pro Asp Cys Arg Phe Leu Thr Ile His Arg Gly Gln Val Val Tyr Val
        35                  40                  45

Phe Ser Lys Leu Lys Gly Arg Gly Arg Leu Phe Trp Gly Gly Ser Val
    50                  55                  60

Gln Gly Asp Tyr Tyr Gly Asp Leu Ala Ala Arg Leu Gly Tyr Phe Pro
65                  70                  75                  80

Ser Ser Ile Val Arg Glu Asp Gln Thr Leu Lys Pro Gly Lys Val Asp
                85                  90                  95

Val Lys Thr Asp Lys Trp Asp Phe Tyr Cys Gln
                100                 105

<210> SEQ ID NO 2
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (7)..(23)
<223> OTHER INFORMATION: Any amino acid
<220> FEATURE:
<221> NAME/KEY: MOD_RES
<222> LOCATION: (25)..(36)
<223> OTHER INFORMATION: Any amino acid
<220> FEATURE:
<221> NAME/KEY: MOD_RES
<222> LOCATION: (38)..(50)
<223> OTHER INFORMATION: Any amino acid and this region may encompass 11
      to 13 residues
<220> FEATURE:
<221> NAME/KEY: MOD_RES
<222> LOCATION: (52)..(69)
<223> OTHER INFORMATION: Any amino acid and this region may encompass 7
      to 18 residues
<220> FEATURE:
<221> NAME/KEY: MOD_RES
<222> LOCATION: (71)..(74)
<223> OTHER INFORMATION: Any amino acid
<220> FEATURE:
<221> NAME/KEY: MOD_RES
<222> LOCATION: (76)..(96)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
```

<223> OTHER INFORMATION: see specification as filed for detailed
      description of preferred embodiments

<400> SEQUENCE: 2

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Cys Xaa Xaa Xaa Xaa Xaa Xaa Xaa
            20                  25                  30

Xaa Xaa Xaa Xaa Val Xaa Xaa Xaa Xaa Xaa Xaa Xaa Xaa Xaa Xaa
        35                  40                  45

Xaa Xaa Trp Xaa Xaa Xaa Xaa Xaa Xaa Xaa Xaa Xaa Xaa Xaa Xaa
    50                  55                  60

Xaa Xaa Xaa Xaa Xaa Phe Xaa Xaa Xaa Xaa Val Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Cys Xaa

<210> SEQ ID NO 3
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: MOD_RES
<222> LOCATION: (27)..(38)
<223> OTHER INFORMATION: Any amino acid
<220> FEATURE:
<221> NAME/KEY: MOD_RES
<222> LOCATION: (40)..(41)
<223> OTHER INFORMATION: Any amino acid
<220> FEATURE:
<221> NAME/KEY: MOD_RES
<222> LOCATION: (44)..(52)
<223> OTHER INFORMATION: Any amino acid and this region may encompass 7
      to 9 residues
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (57)..(69)
<223> OTHER INFORMATION: Any amino acid and this region may encompass 5
      to 13 residues
<220> FEATURE:
<221> NAME/KEY: MOD_RES
<222> LOCATION: (74)..(76)
<223> OTHER INFORMATION: Any amino acid

```
<220> FEATURE:
<221> NAME/KEY: MOD_RES
<222> LOCATION: (78)..(95)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<223> OTHER INFORMATION: see specification as filed for detailed
      description of preferred embodiments

<400> SEQUENCE: 3

Lys Xaa Cys Xaa Asp Xaa Glu Cys Xaa Xaa Xaa Xaa Xaa Xaa Xaa Xaa
1               5                   10                  15

Xaa Xaa Xaa Asp Xaa Xaa Xaa Pro Asp Cys Xaa Xaa Xaa Xaa Xaa Xaa
            20                  25                  30

Xaa Xaa Xaa Xaa Xaa Xaa Val Xaa Xaa Lys Leu Xaa Xaa Xaa Xaa Xaa
        35                  40                  45

Xaa Xaa Xaa Xaa Trp Xaa Gly Ser Xaa Xaa Xaa Xaa Xaa Xaa Xaa Xaa
    50                  55                  60

Xaa Xaa Xaa Xaa Xaa Gly Tyr Phe Pro Xaa Xaa Xaa Val Xaa Xaa Xaa
65                  70                  75                  80

Xaa Xaa Xaa Xaa Xaa Xaa Xaa Xaa Xaa Xaa Xaa Xaa Xaa Xaa Xaa Asp
                85                  90                  95

Phe Xaa Cys Xaa
            100

<210> SEQ ID NO 4
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (35)..(35)
<223> OTHER INFORMATION: Any amino acid
```

```
<220> FEATURE:
<221> NAME/KEY: MOD_RES
<222> LOCATION: (37)..(41)
<223> OTHER INFORMATION: Any amino acid
<220> FEATURE:
<221> NAME/KEY: MOD_RES
<222> LOCATION: (44)..(50)
<223> OTHER INFORMATION: Any amino acid
<220> FEATURE:
<221> NAME/KEY: MOD_RES
<222> LOCATION: (52)..(52)
<223> OTHER INFORMATION: Any amino acid
<220> FEATURE:
<221> NAME/KEY: MOD_RES
<222> LOCATION: (56)..(67)
<223> OTHER INFORMATION: Any amino acid
<220> FEATURE:
<221> NAME/KEY: MOD_RES
<222> LOCATION: (72)..(93)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<223> OTHER INFORMATION: see specification as filed for detailed
      description of preferred embodiments

<400> SEQUENCE: 4

Lys Xaa Cys Xaa Asp Xaa Xaa Cys Xaa Xaa Xaa Xaa Xaa Xaa Xaa
1               5                   10                  15

Ala Xaa Xaa Asp Xaa Xaa Xaa Pro Asp Cys Arg Phe Xaa Xaa Xaa
            20                  25                  30

Xaa Gly Xaa Val Xaa Xaa Xaa Xaa Xaa Lys Leu Xaa Xaa Xaa Xaa
        35                  40                  45

Xaa Xaa Trp Xaa Gly Ser Val Xaa Xaa Xaa Xaa Xaa Xaa Xaa Xaa
    50              55                  60

Xaa Xaa Xaa Gly Tyr Phe Pro Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Asp Phe Xaa
            85                  90                  95

Cys Gln
```

DRIED RECONSTITUTED VESICLE FORMATION FOR PHARMACEUTICAL APPLICATION

CROSS-REFERENCE TO RELATED APPLICATION

The instant application Ser. No. 12/419,167 filed on Apr. 6, 2009, is a Continuation of International Application No. PCT/EP2007/008659, filed Oct. 5, 2007, which claims priority to EP Application No. 06021093.7, filed Oct. 6, 2006, the disclosures of the prior applications are hereby incorporated in their entirety by reference.

The present invention relates to dried reconstituted vesicle (DRV) compositions and water based formulations thereof, which contain one or more therapeutic agents (e.g. hydrophilic protein). More particularly, it relates to DRVs comprising at least one lipid and a fusion promoting agent which after reconstitution form large multilamellar liposomes encapsulating an active agent in an aqueous phase.

Liposomes are known to be useful as carriers of biologically and therapeutically active compounds which facilitate the delivery of these compounds to the body. Liposomes generally comprise an enclosed lipid droplet having a core typically containing a compound in an aqueous medium. In certain embodiments, the compound is chemically bound to a lipid component or simply contained within the aqueous inside compartment of the liposome. There are different types of liposomes: multivesicular liposomes (MVLs) with multiple non-concentric internal aqueous chambers within each liposome particle; multilamellar vesicles (MLVs) having a series of substantially spherical shells formed of lipid bilayers interspersed with aqueous layers, ranging in diameter up to 5 μm or larger; large unilamellar vesicles (LUVs) ranging from 600 nm to 1 μm or larger in diameter, which have a lipid bilayer surrounding a large, unstructured aqueous phase; and small unilamellar vesicles (SUVs), which are similar in structure to the LUVs except that their diameter is less than about 0.2 μm.

A variety of methods for preparing liposomes are well known in the art, several of which are described in Liposome Technology $2^{nd}$ Edition in G. Gregoriadis, CRC Press Inc., Boca Raton (1993). Major challenges of liposome technology are a high level of loading of an active agent into the liposome and to make that loading stable during handling and storage. Another challenge is to adapt the release rate of the active agent to specific aims of the liposome formulation. Although the encapsulation of biological material in liposomes has significant potential for drug delivery in humans, the production of encapsulated material on a commercial scale has often been problematic.

Most pharmaceutical applications for parenteral application focus on small liposomes to avoid undesired side effects such as embolism as described for large liposomes. Further, using small liposomes, it seemed to be easier to manufacture a stable product.

There are several known processes for making MLV encapsulated material either on a small scale or on an industrial scale (Rao, "Preparation of Liposomes on the Industrial Scale. Problems And Perspectives," in Liposome Technology $2^{nd}$ Edition in G. Gregoriadis, CRC Press Inc., Boca Raton, pp 49-65 (1993)). In most cases, a thin lipid film is deposited from an organic solvent on the walls of a container, an aqueous solution of the material to be encapsulated is added, and the container is agitated. This process results in encapsulation of the active agent into MLVs. The main disadvantage of such a process is the variation in encapsulation and often low and not reproducible entrapment of the biological agent into the liposomes in addition to degradation of the biological agent and storage instability of the liposomal suspension.

A method as described in EP0678017 produces freeze and thaw multilamellar vesicles (FATMLVs). The FATMLV method requires that freezing and thawing be done in the presence of the material to be entrapped. However, subjecting sensitive materials such as proteins to such harsh physical manipulation result in inactivation or degradation of the material. In addition, frequent freeze and thaw cycles are not feasible for large scale production and require a high technical operating expense.

It is known that liposomes and their contents may be relatively unstable in an aqueous dispersion. Accordingly, attempts to increase short storage life of a liposomal formulation by dehydration have been the focus of several preparation methods.

Improved passive entrapment and storage of active agent comprising liposomes has been achieved by using a dehydration-rehydration method (EP0485143, WO90/03795, EP0678017 and references therein) in which preformed liposomes are added to an aqueous solution containing an active agent or are mixed with a lyophilized protein, followed by dehydration of the mixture and subsequent rehydration in an aqueous medium. When the solution is dried to a highly viscous lipid mixture, the individual liposomes fuse to form MLVs, which encapsulate the active agent between the lamellae. Upon rehydration, lipid vesicles form, in which the material is encapsulated. This method leads to a rather low encapsulation efficacy dependent on the drug to be encapsulated due to instability of the liposomes, leakage of the active agent or physical inactivation or degradation of the material to be encapsulated.

It is known that the addition of a sugar preserving agent (e.g. bulking agent) prior to dehydration and formation of a dried lipid powder can preserve liposomes involving freeze drying. Bulking agents are described in EP0678017, WO90/03795, WO97/42936, WO92/02208, EP190315 and Liposomes $2^{nd}$ edition, A Practical Approach, edited by Vladimir P. Torchilin and Volkmar Weissig, Oxford University Press (2002). They are used to protect vesicles from damage and leakage of the active agent during freeze drying and avoid fusion of small unilamelar vesicles to large multilamellar structures.

WO97/42936 describes a process for preparing freeze dried MLVs encapsulating an amphiphilic drug composition in addition to sorbitol as a membrane stabilization agent.

WO90/03795 describes the use of cryoprotectants such as a sugar (e.g. sucrose, mannitol, lactose, trehalose, maltose) and at least one protein (e.g. albumin, gelatine or casein) during drying of liposomal preparations to protect the dehydrated product from damage during freeze-drying and subsequent reconstitution, to maintain the liposome bilayer integrity (e.g. little or no fusion or aggregation is observed), and to avoid leakage of the liposomes. Without any lyoprotectants being added, the liposomes completely collapse after drying and rehydration and form MLVs whose contents are largely lost and whose large size prevent proper distribution for systemic applications.

Özer et al. describes the use of cryoprotections such as polyalcohols and saccharides and proteins or amino acids to preserve the structure and integrity of membrane bilayers and to prevent vesicle fusion and aggregation by dehydration and freezing (Özer, Y. et al. (1988) Influence of Freezing and Freeze-drying on the Stability of Liposomes Dispersed in Aqueous Media. Acta Pharm. Technol. 34: 129-139).

EP0560138 discloses dried reconstituted liposomes for inclusion of lipophilic substances such as Nifedipin and methods for preparing those liposomes comprising phospholipid, antioxidants, a cryoprotector and a pH stabilizer. However, the disclosed methods are detrimental for active agents such as proteins. Cryoprotectors such as reducing sugars (e.g. glucose) modify proteins by chemical reaction and lead to the formation of small vesicles e.g. of an average diameter of 40 to 200 nm.

U.S. Pat. No. 5,290,563 discloses a method of encapsulation of heterogeneous substances such as protidic allergens and/or allergenic extracts into liposomes comprising at least one ionic lipid without adding cryoprotective agents. The presence of such heterogeneous substances stabilizes the liposomes.

Kim et al. teaches to prepare liposomes by evaporation of organic solvents from chloroform-ether spherules suspended in water (Kim, S. et al. (1983) Preparation of multivesicular liposomes. Biochim. Biophys. Acta 728: 339-348).

Cruz et al. and references therein teach liposomes as carrier systems for proteins. The methods disclosed have similar disadvantages as described above e.g. use organic solvents, lead to a low encapsulation efficacy or can not be used for large scale manufacturing (Cruz, M. E. et al. (1989) Liposomes as carrier systems for proteins: factors affecting protein encapsulation. Liposomes in the Therapy of Infectious Diseases and Cancer 417-426).

WO2007/067784 relates generally to liposomal pharmaceutical compositions, which contain one or more hydrophobic therapeutic agents (e.g. drugs). However, WO2007/067784 does not address the problem of protein encapsulating liposomes. In fact it teaches the use of cryoprotectants, which stabilize lipid membranes and/or prevent formation of MLVs after rehydration.

Therefore, it is an object of the present invention to provide a method for preparing protein encapsulating liposomes in a dried form which can be rehydrated and which are useful for large scale manufacturing.

It is another object of the present invention to provide liposome preparations which can be rehydrated, stored for extended periods of time while dehydrated, and which after reconstitution turn into a dispersion of multilamellar vesicles with active agent encapsulated in the aqueous phase of the liposomes.

It is another object of the present invention to avoid the need of several freeze and thaw steps for manufacturing of active agent encapsulating MLVs to prevent destruction or inactivation of the active agent.

It is another object of the present invention to provide a method for dehydration of liposomes and for storage as dried lipid formulation in the presence of an active agent, which dried lipid formulation can then be rehydrated by addition of an aqueous solution to form multilamellar liposomes with a high encapsulation rate of the active agent, whereby a convenient reconstitution of the dried product is possible.

It is another object of the present invention to provide a method for large scale production of dried reconstituted MLVs, which is simple, feasible and inexpensive.

It is another object of the present invention to provide dried reconstituted vesicles with a size of more than 1 μm for treatment of diseases e.g. bone and/or cartilage diseases such as osteochondral defects and osteoarthritis.

It is another object underlying the present invention to provide a manufacturing process for liposomes which enables a high encapsulation efficacy of a hydrophilic protein, which avoids organic solvents or detergents, which can be easily carried on a large scale, which produces a stable product upon storage without destruction of the protein, which allows for a sustained release of the protein and which provides liposomes which are large enough to avoid rapid clearance from the site of application.

In one aspect, the invention relates to a dried pharmaceutical composition comprising freeze dried active agent comprising vesicles comprising a) at least one lipid, b) at least one active agent, c) a fusion promoting agent, and d) no membrane stabilizing agent, wherein rehydration of the dried pharmaceutical composition results in the formation of multilamellar liposomes having an average liposomal diameter of more than 1 μm, which liposomes encapsulate the active agent.

The dried pharmaceutical composition according to the invention can be stably stored over long periods of time. Preferably, the dried pharmaceutical composition of the invention is a freeze dried composition. While the composition in dried or freeze dried form is stable, it can be easily reconstituted by adding an aqueous solution. The addition of an aqueous solution results in the formation of multilamellar liposomes having an average liposomal diameter of more than 1 μm, preferably of about 1.5 μm or larger. In these multilamellar liposomes, the active agent is encapsulated with a high encapsulation efficiency of preferably at least 40%, in particular, of at least 50%, more preferably of at least 55%, even more preferably of at least 60% and most preferably of at least 80%.

The composition of the dried pharmaceutical composition of the invention comprises at least one lipid, at least one active agent, at least a fusion promoting agent and no membrane stabilizing agent. Preferably the at least one active agent is a protein, in particular, a hydrophilic protein or an active fragment thereof. Particularly preferred are proteins which are a bone and/or cartilage regeneration agent, preferably CD-RAP. Preferred fusion promoting agents are alkaline amino acids, in particular, selected from arginine, histidine, lysine or citrulline. Further, it has been found that is advantageous to provide the dried pharmaceutical composition containing no membrane stabilizing agent, i.e. in particular, in the absence of a protective sugar, sugar alcohol or glycoside. Further, in some preferred embodiments of the invention, the composition also comprises an inorganic or organic anion such as succinate, fumarate, citrate, malate, phosphate, acetate or chloride.

The dried pharmaceutical composition preferably is a sterile composition.

Without encapsulation with liposomes, even large proteins are rapidly cleared from the site of application e.g. cleared from the synovial fluid through the synovial membrane and will therefore not be available sufficiently for inducing regeneration of defected tissues like cartilage or bone. To extend local retention time of an active agent such as a growth factor at the place of application e.g. the disc or its surrounding and/or within the articular joint the inventors were able to provide a liposomal formulation of a protein e.g. a hydrophilic protein such as CD-RAP or BMP comprising of large multilamellar vesicles (MLVs) with high entrapment and controlled release of the protein.

The inventors provide a parenteral pharmaceutical composition comprising a lyophilized protein liposome composition which is stable against breakdown on long-term storage and which can be reconstituted to produce large multilamellar liposomes comprising a hydrophilic protein. The dried reconstituted vesicles used herein are for example dry granular products, which upon addition of an aqueous medium disperse to form a multilamellar liposomal formulation comprising the biological active component. Advantageously, the stability problems such as aggregation or oxidation of the active agent are avoided by using dried liposomes according to the invention. In addition, a high encapsulation efficacy of hydrophilic ingredients such as proteins like bone- and/or cartilage regeneration agents including BMPs and/or CD/RAP was achieved. In contrast to the prior art, the inventors are now able to provide a stable pharmaceutical composition with minor alteration of the active agent forming a stable lyo cake which can easily and quickly be reconstituted by an aqueous medium with reproducible inclusion entrapment of the active agent, improved stability on storage and a significant increase in the size distribution of multilamellar liposomes when being rehydrated.

The rehydrated liposomes of the invention possess a prolonged resistance in situ after injection e.g. into the synovial fluid, intraarticular space, disc or disc surrounding and thus overcome the limitations of the current state of the art in the field of treatment of cartilage disease. The protein has an immediate action due to the presence of active agent outside the liposome and a delaying or sustained effect upon degradation of the liposomes. The presence of active agent for a long time enables a continued beneficial effect on cells such as chondrogenic and synovial cells, production of proteoglycans, thereby ensuring a regenerative effect or slow down of the disease progression mediated by the active agent. When administering the resulting formulation of the present invention into the affected joint (e.g. osteoarthrotic joint) the resulting formulation can exploit a protective effect on the structure of the joint and an anti-inflammatory and/or regenerative effect mediated by the active agent, a lubricating effect of the liposome, a visculosupplementary effect and/or an effect of substitution of the synovial fluid.

Also within the scope of the present invention is a process for the preparation of a dried liposome composition which after rehydration with an aqueous solution forms multilamellar liposomes with an average liposomal diameter of more than 1 μm encapsulating an active agent, comprising the steps of a) hydratization of a lipid, lipid mixture or lipid film in the absence of an organic solvent, b) generation of small unilamellar vesicles preferably with an average diameter between 50 and 200 nm, c) addition of an aqueous solution of an active agent, d) after, before or together with step c), addition of a fusion promoting agent and optioncally of an inorganic or organic anion, and e) dehydration of said lipid dispersion without the addition of a membrane stabilizing agent.

The small unilamellar vesicles prepared in step b) preferably have an average diameter of at least 50, in particular, of at least 60 and more preferably of at least 70 nm and a maximum diameter of preferably 200 nm, in particular, 150 nm, and more preferably 120 nm.

A particular advantage of the process of the present invention is that the sterile filtration can be performed after steps b) and c). Thus, a sterile dried pharmaceutical composition can be provided.

After preparation of step a) and d), the formulations can be stored e.g. under vacuum at 4° C., preferably at room temperature.

Due to the size of MLV liposomes and due to the thermosensitivity of many active agents such as proteins, sterile filtration or terminal sterilization of known such pharmaceutical preparation is not feasible. These hurdles were overcome with the aseptic manufacturing process according to the invention.

The invention therefore further provides a process for the preparation of an administrable liposome composition comprising multilamellar liposomes with an average liposomal diameter of more than 1 μm encapsulating an active agent, comprising the steps of a) hydratization of a lipid, lipid mixture or lipid film in the absence of an organic solvent, b) generation of small unilamellar vesicles preferably with an average diameter between 50 and 200 nm, c) addition of aqueous solution of an active agent, d) after, before or together with step c), addition of a fusion promoting agent and optionally of an inorganic or organic anion, e) dehydration of said lipid dispersion without the addition of a membrane stabilizing agent, f) rehydration with an aqueous solution and formation of multilamellar vesicles having an average liposomal diameter of more than 1 μm encapsulating the active agent, wherein a step of sterilfiltration is performed after step b) and/or c).

In particular, using a sterile aqueous solution in step f), a sterile composition comprising MLV liposomes can be obtained.

Also encompassed is the provision of a kit comprising a dried pharmaceutical composition as described herein and, in particular, in claim 1 and an aqueous solution for rehydration of the dried pharmaceutical composition.

In the prior art lyoprotectants are described if freeze-drying is desired. Disaccharides, such as sucrose, lactose and trehalose are the most preferred lyoprotectants. Monosaccharides such as glucose or sorbitol or excipients with a low molecular weight such as amino acids and inorganic salts should be avoided, because of their low transition and collapse temperature in the frozen state (Liposomes $2^{nd}$ edition, A Practical Approach, edited by Vladimir P. Torchilin and Volkmar Weissig, Oxford University Press, page 157 (2002)). However, the inventors found that using alkaline amino acids, e.g. arginine as bulking agents does not protect vesicles during freeze drying but, surprisingly, promotes the fusion process which is essential for obtaining multilamellar vesicles with diameters of 1 μm and larger. In addition to this effect, the use of these amino acids surprisingly supports the stability of the formulated protein during freeze drying. The conjunction of these two effects—on the one hand the destabilisation of lipid membranes and on the other hand the stabilisation of drugs was until now totally unknown.

In contrast to prior art liposomes such as MVLs described for example by Kim et al. (Kim, S. et al. (1983) Preparation of multivesicular liposomes. Biochim. Biophys. Acta 728: 339-348), the advantage of the present liposomes is to avoid organic solvents such as chloroform. The liposome preparations of the invention are preferably free of organic solvents and contain, in particular, less than 2 wt %, preferably less than 1 wt %, more preferably less than 0.1 wt % and most preferably 0% organic solvent.

Further, the invention provides for the establishment of a large scale manufacturing method for manufacturing dried reconstituted vesicles which form MLVs upon rehydration for pharmaceutical applications.

An advantage of the method of the invention is that additional liposomal purification steps which are described in prior art methods to remove material that was not entrapped into the aqueous liposomal core or between the liposomal shells can be avoided. It is rather an advantage that a portion of non-incorporated protein which is preferably non-covalently attached to the surface of the liposomes, enables an initially rapid release of the active agent e.g. free protein upon administering the pharmaceutical composition to a subject in need thereof.

A further advantage of the method of the present invention is a high encapsulation of protein (e.g. CD-RAP) in MLVs using the method of the present invention compared to a lower encapsulation efficacy of MLVs manufactured by prior art methods. Furthermore, with the use of the process of the present invention multilamellar liposomes are formed instead of large unilamellar liposomes of state of the art methods such as reconstitution of the freeze dried lipid powder with protein solution.

The term "multilamellar vesicles (MLVs)" means liposomes containing multiple lipid bilayers forming two or more shells, particularly to biphasic multilamellar lipid vesicles. The biphasic lipid vesicles comprise a plurality of spaced apart lipid bilayers comprising a liposome-forming component and optionally a biological active agent. The lipid vesicles comprise peripheral aqueous solution compartments formed between the lipid bilayers and a central core compartment comprising the aqueous solution optionally including an active agent.

The terms "encapsulation, entrapment or trapment" are used herein for the arrangement of substances, in particular, hydrophilic substances in the aqueous core or between two neighbouring shells of a liposome. The quantity of material entrapped inside liposomes can be determined by methods known in the prior art such as purification by centrifugation as described in Liposomes $2^{nd}$ edition, A Practical Approach, edited by P. Torchilin and Volkmar Weissig, Oxford University Press (2002), dialysis as described in Liposomes, A Practical Approach edited by R. R C. New, IRL Press (1990) or those methods as described in the Examples of the invention.

By "without the addition of a membrane stabilizing agent" it is meant that no substance is added or present in an amount to inhibit fusion of liposomal fragments or vesicles e.g. to inhibit the formation of multilamellar vesicles. Examples of membrane stabilizing agents are protective sugars, sugar alcohols or glycosides at a protective concentration at the inside and/or outside surfaces. At a concentration of 50 mM sugar such as trehalose, vesicles are generally the same size as prior to dehydration. At sugar concentrations, e.g. trehalose concentrations of 125 mM or greater, there is nearly no discernable structural difference between vesicles before or after dehydration. However, small amounts of such membrane stabilizing agent might be encompassed if they do not inhibit fusion of the liposomes upon drying e.g. formation of MLVs. Membrane stabilizing agents are preferably present in the inventive composition in an amount of ≤5% (w/v), preferably ≤2.5% (w/v), more preferably ≤1% (w/v), even more preferably ≤0.1% (w/v) and most preferably 0% (w/v).

An "active agent, biological active agent or biological active compound" shall mean any agent that has a therapeutic, biological, pharmacological, pharmaceutical (e.g. treats, controls, ameliorates, prevents, delays the onset of, reduces the risk of developing one or more disease, disorders or conditions or symptoms thereof) and/or cosmetic effect. The therapeutic effect may be local or systemic and may be objective or subjective. Preferably an active agent is a protein, in particular, a hydrophilic protein, more preferably a bone and/or cartilage regeneration protein.

A "membrane stabilizing agent" shall mean an agent that when added at a certain concentration or concentration range protects liposomes from destruction or leakage of the active agent encapsulated while being dried. It may be a protective sugar, sugar alcohol or glycoside, in particular, a mono- or disaccharide or an aminoglycoside. Protective sugars and glycosides include excipients such as trehalose, maltose, sucrose, glucose, lactose, dextran, streptomycin and dihydrostreptomycin.

A "fusion promoting agent" promotes or enables fusion of lipid assemblies to MLVs. Additionally, a fusion promoting agent preferably means an excipient or component which stabilizes the native structure of the active agent e.g. protein. Further, a fusion promoting agent preferably does not protect SUVs during drying or from disruption of SUV lipid bilayers, e.g. by formation of ice crystals. A fusion promoting agent can be an amorphous or partial crystallizing substance or a buffer substance, which leads to fragmentation, rupture or opening of lipid membranes during a dehydration process such as freeze drying to enable encapsulation of an active agent while forming MLVs by subsequent rehydration. Such substances include amino acids, in particular, alkaline amino acids and preferably arginine, histidine, citrulline, lysine and the corresponding salts such as phosphate, sulfate or chloride or mixtures thereof. Preferably, the fusion promoting agent is added in an amount sufficient to enable isotonic conditions after rehydration of the dried liposomal formulation (dried reconstituted vesicles, DRVs). In addition, the fusion promoting agent preferably has no negative impact (e.g. oxidation) on the active agent, e.g. the protein to be encapsulated.

The term "degenerative disc disease (DDD)" is a chronic process characterized in part by progressive loss of proteoglycan and water content in the nucleus pulposus that can become manifest in multiple disorders such as idiopathic low back pain, disc herniation, internal disc disruption or fissured discs, radiculopathy, spinal stenosis, herniated nucleus pulposus-induced sciatica, sciatica, idiopathic scoliosis and/or myelopathy. The disc degeneration grade can be ranked by analysis of preoperative MRI.

For the purpose of the present invention, the term "transdiscally" includes but is not limited to injection into an intervertebral disc, in particular, into the nucleus pulposus (NP) of an intervertebral disc which includes an intact disc, a degenerated disc of different stages, a herniated disc, a ruptured disc, a delaminated disc or a fissured disc. If the volume to be injected might cause pressure of the NP, at least part of the NP can be removed prior to injection or application of the implant for the spinal column. In some cases the volume of the removed material is about the amount of volume ±20% to be applied. The term transdiscally also includes an injection into the annulus fibrosus (AF) of a degenerating or intact disc as described above for the NP. In instances of applying a larger size of a carrier material partial or total removement of the disc might be necessary before application of the pharmaceutical composition according to the invention. It further includes providing the implant into a location outside but closely adjacent to the AF wall or endplate of an adjacent vertebral body, this might avoid the puncture of the AF and therefore potential burden on the disc.

The term "lipid", when used herein, is intended to designate any substance that can be used for the preparation of lipid bilayers. Typical lipids include glycolipids, lecithin, phospholipids, ceramides and mixtures thereof.

Suitable lipids, hydrogenated or not, which are present individually or in mixtures according to the present invention include neutral or positively charged lipids such as natural lecithins or phospholipids. Example of lipids are phosphatidylcholin (PC), egg phosphatidylcholin (EPC), phosphatidylserin (PS), cholesterol (Chol), distearoylphosphatidylcholine (DSPC), sphingomyelin (SM), dioleylphosphatidylcholine (DOPC), dioleylphosphatidylglycerol (DOPG), dilauroylphosphatidylcholin (DLPC), phosphatidylglycerol (PG), dimyristoylphllosphatidylcholine (DMPC), dipamlitoylphosphatidylcholine (DPPC), gangliosides, ceramides, phosphatidyinositol (PI), phosphatic acids (PA), dicetylphosphate (DcP), dimyrylstoylphosphatidylcholine (DMPC), ganglioside and other glycolipids, stearylamine, dipalmritoylphosphatidylgycerol (DPPG), and other synthetic or semi-synthetic lipids. Phospholipids may be natural lipids derived from egg yolks, soy beans or other animals or plants such as yolk lecithin, soy lecithin and the like. The liposomal formulation is typically a mixture of at least one, more preferably at least two lipids such as cholesterol and phosphatidylcholine and more preferably three or more lipids.

In a further preferred embodiment, lipids comprise less than 20, 15, 10, 8, 5, 3, 1 weight percent (wt %) of unsaturated lipids based on the total lipid amount. Preferably the lipids are saturated neutral lipids.

Unsaturated and/or neutral lipids are preferred lipids according to the present invention to increase the stability of the liposomes formed and to improve the sustained release for pharmaceutical application for the purpose of the invention as described within the specification. Unsaturated lipids have a very low transition temperature. Since the lipids will be in a liquid crystalline phase during all phases of production the handling e.g. the dispersion or rehydration to liposomes is much easier and faster. If the ambient temperature is near or crosses the phase transition temperature of lipids the result would be a strong loss of the incorporated compound.

Preferably, the parenteral pharmaceutical compositions described above comprise two lipids, preferably two neutral lipids, more preferably phosphatidylcholin (PC) and cholesterol (Chol). Preferably, the weight percent ratio of the two lipids (e.g. PC:Chol) based on the total lipid amount can be from about 2 to about 7, about 2 to about 6, about 2 to about 5, about 3 to about 7, about 3 to about 6, about 3 to about 5, about 2.7 to about 5.4, about 2.8 to about 5.2, about 2.8 to about 4.2, about 2.8 to about 3.2 (e.g. 3, 4 or 5).

Although it is described that neutral lipids often yield aggregates of MLVs no aggregation could be observed for MLVs of the present invention.

Preferably the lipid mix is charged. Examples of cationic lipids include dioctadecyldermethylammonium chloride (DOPAC), N-(2,3-dioleyloxy)propyl-N,N,N-trimethylammonium (DOTMA), didodecylammonium bromide (DDAB), 1,2-dioleoyloxy-3-trimethylammonio propane (DOTAP), 3-N—(N',N',-dimethylaminoethane)-carbarmol cholesterol (DC-Chol), 1,2-dimyristoyloxypropyl)-dimethylhydroxyethyl ammonium (DMRIE), 2,3-dioleyloxy-N-[2 (sperminecarboxamido)ethyl]-N,N-dimethyl-1-propanaminum trifluoroacetate (DOSPA) and the like.

Examples of anionic lipids are well known to those skilled in the art and include but are not limited to cardiolipin, ascorbylpalmitate, distearoylphosphatidylglycerol (DSPG), phosphatidic acid and phosphatidylserine (PS). Other anionic lipids include amides of phosphatidyl ethanolamine such as anandamides and methanandamides, phosphatidyl serine, phosphatidyl inositol and fatty acid esters thereof, phosphatidyl ethylene glycol, acidic lysolipids, palmitic acid, stearic acid, arachidonic acid, oleic acid, linolenic acid, linoleic acid, myristic acid, sulfolipids and sulfatides, free fatty acids, both saturated and unsaturated, and negatively charged derivatives thereof. More preferably, the anionic lipid is a phosphatidic acid, a phosphatidyl glycerol, a phosphatidyl glyercol fatty acid ester, a phosphatidyl ethanolamine anandamide, a phosphatidyl ethanolamine methanandamide, a phosphatidyl serine, a phosphatidyl inositol, a phosphatidyl inositol fatty acid ester, a cardiolipin, a phosphatidyl ethylene glycol, an acidic lysolipid, a sulfolipid, a sulfatide, a saturated free fatty acid, an unsaturated free fatty acid, a palmitic acid, a stearic acid, an arachidonic acid, an oleic acid, a linolenic acid, a linoleic acid or a myristic acid. Any of the anionic lipids described herein may be fluorinated by replacing at least one hydrogen atom with a fluorine atom.

For improved encapsulation of a water soluble substance such as CD-RAP, the lipid components are preferably selected so that at least one lipid is charged to increase the encapsulation of the active agent. Therefore, in another embodiment, the parenteral pharmaceutical composition comprises up to 20%, 15%, 10%, 5%, 2%, 1%, between about 10% and 1%, between about 5% and 1%, between 0.1% and 0.5% (w/w) charged lipids based on the total lipid amount.

Preferably the charged lipid is cardiolipin or ascorbylpalmitate, preferably between 0.1% and 5% (w/w) of total lipid, between 0.1% and 3% (w/w), between 0.1% and 1.5% (w/w), between 0.1% and 1% (w/w) cardiolipin or ascorbylpscorbylpalmitate of total lipid.

A preferred example of a suitable lipid mixture is phosphatidylcholin (PC), cholesterol (Chol) and ascorbylpalmitate, preferably PC:Chol:ascorbylpalmitate in a ratio of 60%-1%:0%-40%:0%-5%, more preferably in a ratio of 70%-90%:7%-30%:0.1%-3% and most preferably in a ratio of 70%-80%:20%-28%:0.1%-1.5% (w/w) of total lipid content.

Contrary to what was expected from the state of the art which teaches that charged phospholipid species may be important to reduce the size of liposomes (Liposomes $2^{nd}$ edition, A Practical Approach, edited by Vladimir P. Torchilin and Volkmar Weissig, Oxford University Press (2002), page 7 first paragraph) and might have a negative effect on substance retention after freeze-drying/rehydration, the inventors surprisingly found that the addition of a charged lipid increases the size of MLVs after reconstitution (cf. FIG. 3).

The liposomes may further include a lipid derivatized with a hydrophilic polymer to form lipopolymers. Such lipopolymers preferably comprise lipids modified at their head group with a polymer either by a covalent or non-covalent bond. The lipopolymer may be introduced into the liposome either by adding the lipopolymer to a lipid mixture forming the liposome or by first preparing a liposome and then incorporating the lipopolymer to the outer layer of the pre-formed liposome. Lipopolymers are for example described in WO2006/027786 incorporated herein by reference.

A protein according to the invention comprises for example a hydrophilic protein.

Preferably hydrophilic proteins are cartilage or bone regeneration agents e.g cartilage promoting agents or bone morphogenetic proteins. Such agents, in particular, comprise members of the TGF-β family (transforming growth factor, Roberts and Sporn, Handbook of Experimental Pharmacology 95 (1990), page 419-472), the DVR-group (Hötten et al., Biochem. Biophys. Res. Comm. 206 (1995), page 608-613 and further literature cited therein) including BMPs (bone morphogenetic protein, Rosen and Thies, Growth Factors in Perinatal Development (1993), page 39-58) and GDFs (growth differentiation factors), the inhibin/activin (Vale et al., The Physiology of Reproduction, second edition (1994), page 1861-1878), the GDNF, the SOX, the IGF and the EGF protein family.

Interesting members of the TGF-β superfamily or active variants thereof comprise the TGF-β proteins like TGF-β1, TGF-β2, TGF-β3, TGF-β4, TGF-β5 (U.S. Pat. No. 5,284,763; EP 0376785; U.S. Pat. No. 4,886,747; DNA 7 (1988), page 1-8), EMBO J. 7 (1988), page 3737-3743), Mol. Endo. 2 (1988), page 1186-1195), J. Biol. Chem. 265 (1990), page 1089-1093), OP1, OP2 and OP3 proteins (U.S. Pat. No. 5,011,691, U.S. Pat. No. 5,652,337, WO91/05802) as well as BMP-2, BMP-3, BMP-4 (WO88/00205, U.S. Pat. No. 5,013,649 and WO89/10409, Science 242 (1988), page 1528-1534), BMP-5, BMP-6 and BMP-7 (OP1) (Proc. Natl. Acad. Sci. 87 (1990), page 9841-9847; WO90/11366), BMP-8 (OP2) (WO91/18098), BMP-9 (WO93/00432), BMP-10 (WO94/26893), BMP-11 (WO94/26892), BMP-12 (WO095/16035), BMP-13 (WO95/16035), BMP-15 (WO96/36710), BMP-16 (WO98/12322), BMP-3b (Biochem. Biophys. Res. Comm. 219 (1996), page 656-662), GDF-1 (WO92/00382 and Proc. Natl. Acad. Sci. 88 (1991), page 4250-4254), GDF-8 (WO94/21681), GDF-10 (WO95/10539), GDF-11 (WO096/01845), GDF-5 (CDMP1, MP52) (WO95/04819; WO96/01316; WO94/15949, WO96/14335 and WO93/16099 and Nature 368 (1994), page 639-643), GDF-6 (CDMP2, BMP-13) (WO95/01801, WO96/14335 and WO95/16035), GDF-7 (CDMP3, BMP-12) (WO95/01802 and WO95/10635), GDF-14 (WO097/36926), GFD-15 (WO99/06445), GDF-16 (WO99/06556), 60A (Proc. Natl. Acad. Sci. 88 (1991), page 9214-9218), DPP (Nature 325 (1987), page 81-84), Vgr-1 (Proc. Natl. Acad. Sci. 86 (1989), page 4554-4558) Vg-1, (Cell 51 (1987), page 861-867), dosalin (Cell 73 (1993), page 687702), MIS (Cel 45 (1986), page 685-698), pCL13 (WO97/00958), BIP (WO94/01557), inhibin a, activin βA and activin βB (EP 0222491), activin βC (MP121) (WO96/01316), activin βE and GDF-12 (WO096/02559 and WO98/22492), activin βD (Biochem. Biophys. Res. Comm. 210 (1995), page 581-588), GDNF (Science 260 (1993), page 1130-1132, WO93/06116), Neurturin (Nature 384 (1996), page 467-470), Parsephin (Neuron 20 (1998), page 245-253, WO97/33911), Artemin (Neuron 21 (1998), page 1291-1302), Mic-1 (Proc. Natl. Acad. Sci. USA 94 (1997), page 11514-11519), Univin (Dev. Biol. 166 (1994), page 149-158), ADMP (Development 121 (1995), page 4293-4301), Nodal (Nature 361 (1993), page 543.547), Screw (Genes Dev. 8 (1994), page 2588-2601) or combinations thereof. Other useful proteins include biologically active biosynthetic constructs including biosynthetic proteins designed using sequences from two or more known morphogenetic proteins. Examples of biosynthetic constructs are disclosed in U.S. Pat. No. 5,011,691 (e.g. COP-1, COP-3, COP-4, COP-5, COP-7 and COP-16). An example of a useful SOX protein family member (e.g. SOX-9) is disclosed in WO96/17057. The disclosure of the cited publications including patents or patent applications is incorporated herein by reference.

In one embodiment, the cartilage or bone regeneration agent is selected from the group of proteins with an SH3-domain or with a domain which adopts an SH3-like domain fold such as CD-RAP. SH3-domains or SH3-like domains are described for example in Stoll et al. (Stoll, R. et al. (2003) Backbone dynamics of the human MIA protein studied by (15)N NMR relaxation: implications for extended interactions of SH3 domains. Protein Sci. 12: 510-519; Stoll, R. et al. (2001) The extracellular human melanoma inhibitory activity (MIA) protein adopts an SH3 domain-like fold. Embo J 20: 340-349) and can be determined by the prediction of an SH3-fold by an 3D-PSSM Web server published in Kelley et al. (Kelley, L. A. et al. (2000) Enhanced genome annotation using structural profiles in the program 3D-PSSM. J Mol. Biol. 299: 499-520). SH3-domains, also called Src homology domains, are protein molecules that are found in many intracellular proteins. So far, no SH3-domain proteins were described to be useful in treatment of spinal disorders.

In another embodiment the cartilage or bone regeneration agent is a protein which specifically can bind to fibronectin, fibronectin fragments and/or proline rich sequences as for example described in the literature (Stoll, R. et al. (2001) The extracellular human melanoma inhibitory activity (MIA) protein adopts an SF13 domain-like fold. Embo J 20: 340-349; Homandberg, G. A. and Hui, F. (1996) Association of proteoglycan degradation with catabolic cytokine and stromelysin release from cartilage cultured with fibronectin fragments. Arch. Biochem. Biophys. 334: 325-331; Homandberg, G. A. et al. (1997) Fibronectin-fragment-induced cartilage chondrolysis is associated with release of catabolic cytokines. Biochem. J 321 (Pt 3): 751-757).

In one embodiment, the cartilage or bone regeneration agent comprises a fibronectin or integrin binding domain. Binding of the cartilage differentiation and maintenance factor to extracellular proteins such as fibronectin or fibronectin fragments as well as integrins can be determined for example by ELISA. Fibronectin, fragments or integrins thereof can be coated on plastic surfaces and are exposed to the cartilage differentiation and maintenance factor. The amount of binding can be determined by a peroxidase-linked monoclonal antibody against the cartilage differentiation and maintenance factor. Integrin binding can also be determined as described by Bauer et al. herewith incorporated by reference (Bauer, R. et al. (2006) Regulation of integrin activity by MIA. J Biol Chem 281: 11669-11677).

Preferably, the cartilage or bone regeneration agents are defined as a) chondrocyte proteins comprising or having the mature sequence of CD-RAP (SEQ ID No 1) and functional fragments or variants thereof, b) proteins having at least 63% preferably 80%, more preferably 90% amino acid sequence homology with the C-terminal four cysteine skeleton of CD-RAP, amino acids 12 to 107 of SEQ ID No. 1, or c) proteins having any of the generic sequences 1 to 3 defined herein (SEQ ID No 2, 3 and 4).

Functional fragments having the same biological function as CD-RAP preferably have a length of at least 20, in particular, at least 40 and more preferably at least 50, most preferably 80 contiguous amino acids of the sequence shown in SEQ ID NO:1. Preferably, the functional fragments comprise the amino acids from position 1 to 50, 1 to 70, 1 to 80, 20 to 80, 20 to 107 of SEQ ID No 1.

```
Mature CD-RAP sequence
                                         (SEQ ID No 1)
GPMPKLADRKLCADQECSHPISMAVALQDYMAPDCRFLTIHRGQVVYVFS

KLKGRGRLFWGGSVQGDYYGDLAARLGYFPSSIVREDQTLKPGKVDVKTD

KWDFYCQ

Generic sequence 1
                                         (SEQ ID No 02)
C X_4 C X_17 C X_12 V X_{11-13} W X_{7-18} F X_4 V X_21 C X Generic sequence 2
                                         (SEQ ID No 03)
K X C X D X E C X_{11} D X_3 P D C X_12 V X_2 K L X_{7-9} W

X G S X_{5-13} G Y F P X_3 V X_{18} D F X C X
```

-continued

```
Generic sequence 3
                                            (SEQ ID No 04)
K X C X D X2 C X8 A X2 D X3 P D C R F X5 G X V X5

K L X7 W X G S V X12 G Y F P X22 D F X C Q
``` wherein "X" at each occurrence independently represents any amino acid and the number in lowercase the number of any amino acid. Preferably, "X" independently represents a naturally occurring amino acid and, in particular, A, R, N, D, B, C, Q, E, Z, G, H, I, L, K, M, F, P, S, T, W, Y or V.

Particularly preferably, the cartilage or bone regeneration agent is CD-RAP (Cartilage derived retinoic acid sensitive protein), also named MIA (melanoma inhibitory activity), OTOR (fibrocyte derived protein, FDP, MIA-like, MIAL) and TANGO 130 which belongs to a class of secreted proteins (Bosserhoff, A. K. et al. (2004) Characterization and expression pattern of the novel MIA homolog TANGO. Gene Expr. Patterns. 4: 473-479; Bosserhoff, A. K. and Buettner, R. (2003) Establishing the protein MIA (melanoma inhibitory activity) as a marker for chondrocyte differentiation. Biomaterials 24: 3229-3234; Bosserhoff, A. K. et al. (1997) Mouse CD-RAP/MIA gene: structure, chromosomal localization, and expression in cartilage and chondrosarcoma. Dev. Dyn. 208: 516-525; WO00/12762). CD-RAP or MIA is a 130 amino acid protein (EP 0710248, EP 1146897, fully incorporated herein by reference) that is a highly specific marker for chondroid differentiation.

Preferably, the protein according to the invention comprises CD/RAP (MIA), BMP-2, BMP-7, BMP-12, BMP-13, GDF-5 (MP-52), TGF-beta1, TGF beta2, TGF-beta3, TGF-alpha or active fragments or combinations thereof, most preferably CD/RAP (MIA).

The protein contemplated herein can be expressed from intact or truncated genomic DNA or cDNA or from synthetic DNAs, in prokaryotic or eukaryotic host cells. Proteins can be isolated from the culture media or inclusion bodies and/or refold to form biological active compositions. See e.g. EP 0710248 and Lougheed et al. (Lougheed, J. C. et al. (2001) Structure of melanoma inhibitory activity protein, a member of a recently identified family of secreted proteins. Proc. Natl. Acad. Sci. U.S.A 98: 5515-5520) for exemplary protocols for recombinant protein purification of CD-RAP. Detailed description of how to test the activity (e.g. chondrogenesis) of such isolated proteins is described in Tscheudschilsuren et al. and Stoll et al. (Tscheudschilsuren, G. et al. (2005) Regulation of mesenchymal stem cell and chondrocyte differentiation by MIA. Experimental Cell Research 1-10; Stoll, R. et al. (2003) Backbone dynamics of the human MIA protein studied by (15)N NMR relaxation: implications for extended interactions of SH3 domains. Protein Sci. 12: 510-519), the disclosures of which is incorporated by reference herein. A bioassay for cartilage induction is described in example 2 to 5 in EP 1146897, incorporated by reference herewith.

Preferably, the fusion promoting agent is used in an amount sufficient to avoid osmotic stress in a physiological environment and/or to maintain iso-osmolar conditions for parenteral applications. Preferably, the fusion promoting agent is used in an amount of less than 8% (m/v) based on the particulate material before drying, preferably less than 5%, preferably between 2% and 5%.

In a preferred embodiment, the parenteral pharmaceutical composition comprising freeze dried protein containing vesicles comprise the fusion promoting agent in an amount sufficient to form an isotonic liposomal dispersion after rehydration with the aqueous solution. Preferably, the pH of the rehydrated liposomal dispersion is between pH 4 and pH 9, between pH 5 and pH 8, preferably between pH 6 and pH 7.5.

Suitable inorganic or organic anions are e.g. succinate, fumarate, citrate, malat, phosphate, acetate, chloride, preferably phosphate.

Preferably, the fusion promoting agent is arginine phosphate, preferably between 100-800 mM, more preferable 100-600 mM or most preferably 280 and 400 mM arginine phosphate after reconstitution of the lyophilized liposomes.

Other additives or additional substances like antioxidants such as methionine, ascorbic acid, tocopherol, butylhydroxytoluol (BTH), butylhydroxyanisol, propyl gallate, a charged substance such as stearylamine, oleylamine, dicetyl phosphaste or the like can be adjusted appropriately. Preferably the additive is butylhydroxytoluol (BTH), butylhydroxyanisol and/or methionine preferably between 0.1 and 5% (w/w) of total lipid, between 0.1 and 3% (w/w), between 0.1 and 1.5% (w/w), between 0.1 and 1% (w/w) antioxidants e.g. butylhydroxytoluol of total lipid and/or between 5 and 100 mM methionine final concentration of rehydrated liposomes, more preferably between 5 and 50 mM, most preferably between and 25 mM methionine final concentration of rehydrated liposomes. Additional substances can be those which serve to improve the sustained release, increase the half life of the liposomes or target the liposome and hence the drug to a particular tissue or cell type.

In addition to the active agent, the pharmaceutical liposomal composition of the present invention can comprise additional therapeutic or biologically-active agents. For example, therapeutic factors useful in the treatment of a particular indication e.g. osteoarthritis such as one or more inhibitors that are involved in destruction of articular cartilage or synovial components not limited to anti-metalloproteinases, cycline compounds, cytokine antagonists, corticosteroids, TNF inhibitors; IL-inhibitors, anti-angiogenic substances, aggrecanase inhibitors, p38 kinase inhibitors, apoptosis inhibitors, hyaluronidase inhibitors and inhibitors of proteolytic enzymes can be present. Factors that control inflammation including infliximab, etanercept, adalimulab, nerelimonmab, lenercept and the like, or combinations thereof can also be part of the composition. It is also envisaged that the pharmaceutical liposomal composition may include extracellular matrix components such as hyaluronic acid or a derivative thereof including salts, ester, inner ester and sulphated derivates, preferably partial ester of hyaluronic acid.

The invention is also envisaged to cover a parenteral pharmaceutical composition or a process for its preparation according to any of the embodiments of the present invention wherein more than 70%, 80%, 90%, 95%, 98% of liposomes formed upon rehydration with an aqueous solution encapsulation the active agent are multilamellar liposomes. In more detail, the percentage above means that upon rehydration liposomes are formed of which the percentage indicated above represent the portion of the total liposomes formed.

In one embodiment, the aqueous solution is buffered or unbuffered, preferably unbuffered, most preferably water for injection.

In a preferred embodiment, the multilamellar liposomes, which preferably is a liposomal dispersion, has an osmolarity of 200 to 400 mosmol, preferably 250 to 350 mosmol.

In one embodiment, the parenteral pharmaceutical composition according to the invention contains at least 0.125 µmol of the protein, preferably 1.25 pmol of CD-RAP per µmol of liposomal lipid.

In one embodiment multilamellar liposomes according to the invention are prepared by the dehydration and rehydration process as described above containing intra and extra liposomal active agent in a solution, preferably an isotonic solution.

Another preferred embodiment encompasses a pharmaceutical composition comprising freeze dried protein comprising vesicles comprising a) phosphatidylcholin, cholesterol and ascorbylpalmitate in a ratio of about 78-80% to 19.5%-28% to 0.5-2% of total lipids, b) a bone and/or cartilage inducing agent preferably CD-RAP and c) a fusion promoting agent preferably arginine phosphate with a pH between pH 4 and pH 9 preferably pH 5 and pH 8, most preferably pH 6 and pH 7.5, wherein multilamellar liposomes having an internal aqueous space comprising the bone and/or cartilage inducing agent with an average liposomal diameter of more than 1 µm, preferably between 1 µm and 2.5 µm are formed upon rehydration of a dried composition with an aqueous solution encapsulating the active agent.

The processes of the present invention provide a dried liposome composition as well as a reconstituted liposome composition. The dried liposome composition preferably is freeze dried and/or sterile. The reconstituted liposome composition preferably is parenterally administrable and also sterile. In particular, the processes allow for a high encapsulation efficacy and high intraliposomal protein concentration after rehydration in an aqueous medium and formation of multilamear liposomes.

These processes comprise the steps of hydratization of a lipid, lipid mixture or lipid film in the absence of an organic solvent whereby large MLVs are formed and subsequent generation of small unilamellar vesicles or liposomes preferably with an average diameter between 50 and 200 mm, 50 and 150 nm, 50 and 120 nm, 70 and 120 nm.

According to the present invention, a lipid or lipid mixture such as a lipid powder can be hydrated by addition of an aqueous solution. The aqueous solution can be buffered or unbuffered (e.g. buffered or unbuffered protein bulk solution). Preferably, the aqueous solution contains at least 50% (w/w) more preferably at least 90% (w/w) and most preferably at least 99% (w/w) of water. A lipid film can be prepared by dissolution of the lipids in an organic solution such as for example ter-butanol and subsequent drying under nitrogen stream or lyophilization.

Several techniques are available of generating small unilamelar liposomes and sizing liposomes. These methods include a variety of techniques applying a force sufficient to reduce the size of the liposomes and produce smaller unilamellar vesicles. Such methods include homogenization, which fragment large liposomes into smaller ones by shearing. In a typical homogenization procedure the liposomes are recirculated through an emulsion homogenizer until the desired size e.g. an average diameter between 50 and 200 nm, between 50 and 150 nm, between 50 and 120 nm or between 70 and 120 nm is achieved. High pressure homogenizers used for liposome manufacture are for example described in Liposomes $2^{nd}$ edition, A Practical Approach, edited by Vladimir P. Torchilin and Volkmar Weissig, Oxford University Press page 17 (2002). Other methods include extrusion of liposomes through porous polycarbonate membranes under pressure. In generally, the liposomal dispersion is cycled several times through the membrane. Successive smaller pore membranes can be used for gradual reduction of the size. Preferred filters or membranes have a size smaller or equal to 250 nm, 200 nm, 150 nm, 100 um, 80 nm, 50 nm or 15 nm. Preferred passages of cycles are 1, more preferably 2, most preferably 3 or more. Further methods are sonication, microfluidization or mechanical shearing as well as combinations of different methods. The size of the liposomes can be monitored using conventional methods such as light scattering.

After formation of small unilamellar liposomes an aqueous protein solution is added to the generated small unilamellar liposomes. After, before or together with this step a fusion promoting agent is added.

A sterilization step can be included after formation of SUVs and/or after addition of the aqueous protein solution. A sterilisation step e.g. a sterilfiltration can be performed by filtration through a sterile filter with a pore size of 0.22 µm. Examples of such sterile filters are Ultipor N66 (PALL), Acrodisc 4455T (PALL) or Millex GV SLGV025LS (Millipore).

In a preferred embodiment, the concentration of protein is between 25 µg/ml and 10 mg/ml, but more typically between 250 µg/ml and 2.5 mg/ml reconstituted multilamellar liposome preparation.

Preferably, the fusion promoting agent is comprised in the product and processes of the invention in an amount sufficient to form an isotonic liposomal dispersion after rehydration with the aqueous solution, preferably in a concentration between 50 mM to 800 mM, 200 mM to 600 mM and most preferably between 250 mM and 400 mM. Preferably, the pH of the rehydrated multilamellar liposomes and/or liposomal dispersion is between pH 4 and pH 9, more preferably between pH 5 and pH 8, most preferably between pH 6 and pH 7.5.

Dehydration of said lipid dispersion includes lyophilization or freeze drying. It will be appreciated that drying methods other than lyophilization can be used in the invention, for example vacuum drying, drying under a stream of nitrogen, spray, tray, and drum drying. In another embodiment, dehydration of said lipid dispersion is fragmentation, rupture or opening of small unilamellar vesicles by dehydration e.g. by lyophilisation or freeze drying.

Optionally, a further step e.g. filtration step through membranes such as polycarbonate membranes can be included after any of the manufacturing steps described above to eliminate for example crystals of lipophilic substances.

Additives including those described above (e.g. antioxidants, stabilizing agents) can be included at any of the process steps of the present invention.

In dehydrated, i.e. dried, in particular, freeze dried form, the composition can be stably stored over long periods of time.

The dehydrated product (e.g. lyophilized "cake") may then be reconstituted by the addition of destilled water, aqueous or other appropriate solution, buffered or unbuffered. The liposomes can be resuspended or rehydrated in the aqueous solution by gentle swirling of the solution. The rehydration can be performed at room temperature or at other temperature appropriate to the composition of the liposomes and their internal contents. Rehydration of the lyophilized formulation forms a suspension or dispersion of multilamellar liposomes which have an increased size distribution and morphology compared to the original liposomal suspension before drying.

In another preferred embodiment, multilamellar vesicles encapsulating the protein are substantially formed during rehydration of the freeze dried liposome composition (step e), more preferably, wherein the multilamelar liposomes are not formed during dehydration of said lipid dispersion (step d).

Preferably, the trapping efficacy or high incorporation of at least one biological active compound is more than 40%, 55%, more than 60%, more than 70%, more than 80% of the active agent.

The present invention covers pharmaceutical compositions comprising dried reconstitutable vesicles comprising freeze dried protein comprising vesicles and methods of their production with negligible or no detectable aggregation or degradation of the active agent.

In a preferred embodiment, more than 60%, 80%, 90%, 95% or about 100% of the rehydrated MLV liposomes maintain or have a size distribution of larger than 1 µm more preferably between 1.0 µm and 5 µm, between 1.5 µm and 5 µm, between 1.0 µm and 3 µm, most preferably between 1.2 µm and 2.5 µm. Mean vesicle diameters can be determined by electron microscopic examination, photon correlation microscopy, laser light scattering, laser diffraction (e.g. Mastersizer™) or through light obscuration techniques (e.g. Accusizer™) or further methods as described in Liposomes $2^{nd}$ edition, A Practical Approach, edited by Vladimir P. Torchilin and Volkmar Weissig, Oxford University Press (2002) incorporated by reference herewith.

A preferred method is photon correlation microscopy.

A further aspect of the present invention comprises a pharmaceutical freeze dried composition obtainable by a method of the invention as well as a reconstituted pharmaceutical composition obtainable by the methods described herein.

Multilamellar liposomes encapsulating an active agent e.g. a bone and/or cartilage regeneration agents such as CD/RAP can provide benefit in a number of treatment areas such as cartilage regeneration in the case of osteochondral defects, full-thickness defects, partial-thickness effects, arthritis such as osteoarthritis, rheumatoid arthritis, psoriatic arthritis, juvenile chronic arthritis, rhizomelic pseudoarthritis, rheumatoid polyarthritis, synovitis or villonodular synovitis, spinal disorders, degenerative disk disease, tendon and/or ligament induction, tendonitis, meniscus tears and/or anterior crucial ligament (ACL) injury. The advantage of such a liposomal delivery of the active agents is a more efficient, localized delivery to the desired surrounding tissue. The liposomes can be designed to provide a sustained release depot at a targeted site and slow release of the encapsulated drug.

Another advantage of the MLVs of the present invention in contrast to for example SUVs is that in the case of treatment of osteoarthritis via injection into the synovia the drug containing MLVs are restrained at the place of application due to their large size and slowly release the encapsulated active agent.

Therefore, another aspect of the invention is the use of the sterile pharmaceutical freeze dried composition of the invention for manufacturing of a pharmaceutical composition for treatment of a bone and/or cartilage defect, an immunological disease preferably osteoarthritis, rheumatoid arthritis and a spinal disorder such as degenerative disc disease in a subject preferably by one or repeated injections after rehydration of the freeze dried composition with an aqueous solution.

In a preferred embodiment the spinal disorder is idiopathic low back pain, disc herniation, internal disc disruption or fissured discs, radiculopathy, spinal stenosis, herniated nucleus pulposusinduced sciatica, sciatica, idiopathic scoliosis or myelopathy.

In a preferred embodiment, the injection is a local or non-systemic injection, preferably into the synovia, synovia space, nucleus pulposus, nucleus pulposus space, intradiscally or transdically.

The dose scheme can range from a plurality of times weekly to a plurality of times a month, with a preferred interval of not more than once very third day. The total treatment period is preferably at least once a week, more preferably at least once a month.

The pharmaceutical composition can also be suitable for a long-term administration for at least 3 months, for at least 6 months, for at least 12 months, up to 18 months, up to 24 months or even longer.

The pharmaceutical composition of the invention can preferably be administered at a single dose unit of about 0.25 mg up to about 25 mg, especially about 0.5 mg to about 15 mg and more preferably about 5 mg to up to 15 mg of liposomal protein.

A further preferred treatment protocol comprises administering said pharmaceutical composition of the present invention
 a) at least 1 time, especially 1 to 3 times in the first week, followed by an interval of 1 to 5 weeks without administration, and optionally 1 or more repeats of the administration protocol,
 b) once a week or once for several successive weeks, or
 c) once a month or once for several successive months,
wherein the monthly dose is preferably about 1 mg up to about 100 mg, especially about 2 mg to about 60 mg and more preferably about 20 mg to up to 50 mg of liposomal protein.

Liposomal stability on storage is at least three month, preferably at least 6 month, more preferably at least one year.

All references disclosed herein are specifically incorporated by reference thereto in their entireties.

While preferred embodiments have been illustrated and described, it should be understood that modifications can be made in accordance with ordinary skill in the art without departing from the invention in its broader aspect as defined by the claims.

The invention is further described by the enclosed Figures and the following Examples.

EXAMPLES

Example 1

Figure 1:
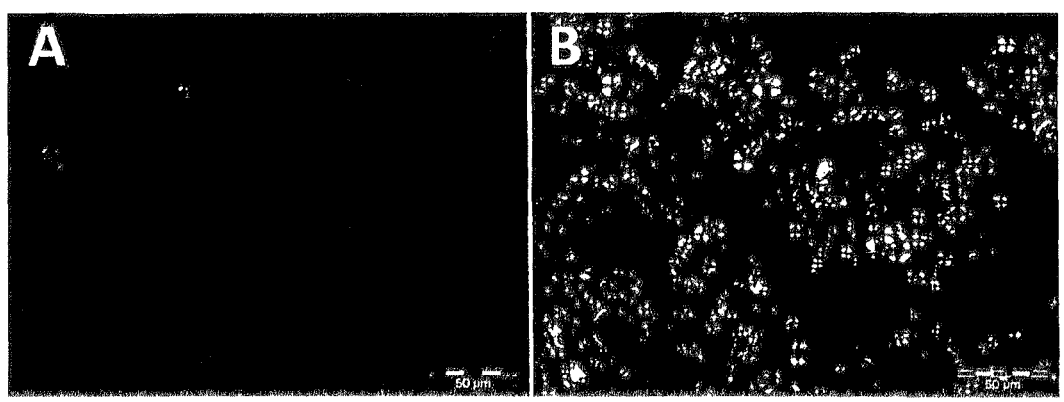
FIG. 1 shows the morphology of liposomes manufactured by the freeze and thaw method (A) according to example 3 in comparison to the method according to example 1 of the invention (B).

Preparation of Freeze Dried Reconstituted Liposomes (DRVs) with a Fusion Promoting Agent A: 750 mg phosphatidylcholine (Lipoid S100), 250 mg cholesterol with or without 10 mg ascorbylpalmitate were solved in 20 ml ethanol in a round bottom flask. The solvent was removed in a rotary evaporator quantitatively. The generated thin lipid film was rehydrated in 10 ml water to get liposomes (10% (w/v) lipid) by gentle stirring at room temperature. Unilamellar vesicles (SUV) were prepared with a diameter of approximately 100 nm by subsequent sonification. 300 µl of SUV were mixed with 250 µl CD-RAP solution (3 mg/ml in 420 mM arginine/$H_3PO_4$ pH 7.5) and lyophilized. The encapsulation takes place during the rehydration of the lyo cake with 300 µl destilled water and gentle vortexing. This led to an entrapment efficacy of more than 40% into MLV with an average diameter of 1.5 µm without chemical alteration of the entrapped drug as determined by HPLC and enzyme linked immunoassays (ELISA).

B: 111.4 g phosphatidylcholine (Lipoid S100), 37.1 g cholesterol and 1.5 g ascorbylpalmitate were solved in 800 ml tert. butanol to get a molecular dispersed mixture. The solvent was removed quantitative by freeze drying. By hydrating the dry lipids with 1.5 L water and vigorous shaking multiple layered liposomes with diameters of several micrometers were formed. The lipid dispersion was homogenized using a high pressure homogenizer and subsequently extruded through a 100 nm membrane to obtain monodispers small unilamellar vesicles (SUV). 3 ml SUV were added to 2.5 ml CD-RAP solution (3 mg/ml in 420 mM arginine/$H_3PO_4$ pH 7.5) and freeze dried. Reconstituting the stable homogeneous lyo cake with 3 ml destilled water and subsequent shaking led to a homogeneous dispersion of multiple layered liposomes (DRV) with a diameter of about 1.5 µm and an encapsulation efficacy of more than 40%.

Example 2

Preparation of DRVs with Different Excipients e.g. Fusion Promoting Agents

The influence of different excipients or additives e.g. fusion promoting agents on the formation of dried reconstituted vesicles (DRVs) comprising a hydrophilic protein e.g CD-RAP useful for treatment of various diseases such as cartilage and bone disease e.g. osteoarthritis, osteochondral defects or degenerative disc disease was analyzed. Instead of using arginine/$H_3PO_4$ pH 7.5 as additives and/or fusion promoting agents according to example 1 several other additives and/or buffering systems were tested and summarized in Table 1. The following parameters were analyzed: size distribution by photon correlation spectroscopy (PCS), osmolarity by osmometer, protein stability by HPLC, visual appearance of the reconstituted vesicles and the encapsulation efficacy.

TABLE 1

Characterization of DRVs with different fusion promoting agents

| Additives | Protein stability | Average size | Dipersion | EE [%] | Physiol. Osmol. |
|---|---|---|---|---|---|
| Trehalose 5% (w/v) | + | − | + | nd | + |
| Trehalose 3% w/v)/ Mannitol 2% (w/v) | + | − | + | nd | + |
| Trehalose 2% (w/v)/ Mannitol 3% (w/v) | + | − | + | nd | + |
| Mannitol 5% (w/v) | + | − | + | nd | + |
| PEG4000 5% (w/v) | + | + | − | nd | + |
| Glycin 1.1% (w/v) | − | + | + | − | + |
| Glycin 1.1% (w/v)/ 20 mM KCl/150 mM KH2PO4 | + | + | + | − | − |
| 350 mM Arginin/ H3PO4/pH 7.5 | + | + | + | + | + |
| 350 mM Histidin/ H3PO4/pH 7.5 | + | + | + | + | + |
| 350 mM L-Lysin/ H3PO4/pH 7.5 | + | + | + | + | + |
| phosphate buffered saline pH 7.4 | − | + | + | nd | + |

The protein stability, the average size of the liposomes, the homogeneous dispersion and the encapsulation efficacy (EE) was determined after rehydration of the dried liposomes.
nd: not determined, parameters were not determined it other requirements were not fulfilled By using trehalose, mannitol and mixtures thereof as cryoprotecting agent a stabilizing effect of both the protein and the liposomal membrane were obtained resulting in unaffected small unilamellar vesicles instead of large MLVs. Another formulation comprised Polyethylenglycol 4000 as cryoprotecting agent which failed the specification of a homogeneous dispersion after rehydrating the lyo cake to liposomes. The application of phosphate buffered saline as well known formulation buffer system, the addition of acetic acid pH 6.0 and pH 4.2 alone could not stabilize the protein in the drying process resulting in a strong destruction of the protein. However, the inventors found that formulations comprising amino acids led to different surprising results. Glycin as additive required the addition of salt for the maintenance of protein stability, but led to a reconstituted liposomal formulation in a non-physiological medium. However, surprisingly the addition of basic amino acids such as but not limited to arginine, histidine and lysine fulfilled all the requirements for getting a homogeneous liposomal solution or dispersion of CD-RAP encapsulated in large multiple liposomes (≥1.5 µm) with a high entrapment efficacy (≥40%) without chemical alteration of the protein during the manufacturing process.

Example 3

Manufacturing Liposomes with the "Freeze and Thaw" Method 742 mg phosphatidylcholine (Lipoid 8100), 248 mg cholesterol and 10 mg ascorbylpalmrnitate were solved in 20 ml ethanol in a round bottom flask. The solvent was removed in a rotary evaporator quantitatively. The generated thin lipid film was rehydrated in 7.8 ml water to get liposomes (12.8% (w/v) lipid) by gentle stirring at room temperature. Unilamellar vesicles (SUV) were prepared with a diameter of approximately 100 nm by subsequent sonification. 234.8 µl of the SUV solution were mixed with 65.2 µl of a CD-RAP solution (1.15 mg/ml in 420 mM arginine/$H_3PO_4$ pH 7.5). The liposomal dispersion got milky after 3 freeze and thaw cycles (cooling down in liquid $N_2$ and subsequent thawing at room temperature) due to fusion of lipid membranes and formation of liposomes. The morphology of the liposomes remained with increased numbers of freeze and thaw cycles e.g. 5 cycles. The product was a viscous milky suspension with an encapsulation efficacy (measured according to example 5 method A) of more than 40%. However, in contrast to the MLVs prepared according to the method of the present invention, the majority of liposomes generated by the freeze and thaw method were only unilamellar. Determination of the lamellarity by light microscopy in double polarized light showed less than 5% malteser crosses (detection parameter in multiple layered liposomes), whereas the liposomes prepared by freeze drying according to the invention (e.g. example 1) led to ≥95% multiple layered liposomes (FIG. 1). The formation of unilamellar liposomes instead of MLVs in case of the freeze and thaw method is further supported by the literature (Liposomes, A Practical Approach edited by R. R. C. New, IRL Press (1990), page 58 last paragraph).

Example 4

Liposomes Manufactured Upon Lipid Powder Reconstitution 750 mg phosphatidylcholine (Lipoid S100), 250 mg cholesterol and 10 mg ascorbylpalmitate were solved in 20 ml ethanol in a round bottom flask. The solvent was removed in a rotary evaporator quantitatively. The generated thin lipid film was rehydrated in 10 ml 200 mM arginine/$H_3PO_4$; pH 7.5 to get liposomes (10% (w/v) lipid) by gentle stirring at room temperature. Unilamellar vesicles (SUV) were prepared with a diameter of approximately 100 nm by subsequent sonication. 3000 µl of SUV were mixed with 2500 µl destilled water and lyophilized. The encapsulation took place during the rehydration of the lipid lyo cake with 3000 µl CD-RAP solution (0.3 mg/ml in 150 mM Arg/PO4 pH 7.5) and gentle vortexing.

The thus generated liposomes were compared to those manufactured according to example 1A. The entrapment efficacy was determined according to example 5A.

Surprisingly, the hydration of the lyophilized lipid cake with CD-RAP solution led to a very poor encapsulation efficacy of 20%±4% of CD-RAP (n=4) while the hydration of the co-lyophilisate of CD-RAP and lipids according to example 1A led to a 3-fold increased encapsulation efficacy of 60%±10% (n=10).

The homogeneous close contact of both lipids and protein dedicated to be entrapped is essential for a high entrapment efficacy which is best reached by co-lyophilisation of the components.

Example 5

Determination of the Encapsulation Efficacy of CD-RAP

Three different methods were used to determine the entrapment efficacy of CD-RAP in liposomes manufactured according to the above examples. Method A was used to separate encapsulated CD-RAP inside the liposomes from non-encapsulated CD-RRAP by centrifugation. Method B determined the encapsulation using a dialysis step. Method C is a modified determination by centrifugation/ultra filtration.
Method A: Determination by Centrifugation Step 100 µl of the rehydrated liposomal solution were diluted very carefully and slowly with 300 µl of water for injection to obtain a difference in density between the lipsomes. A faster dilution resulted in a disruption of the liposomes and in addition to loss of incorporated protein. The dilution step is necessary to create a difference between liposomes and surrounding solvent, which in turn is a necessity for successful spinning down the liposomes. The diluted liposomal solution were centrifuged at room temperature at 16.000 rcf for 15 minutes and resulted in a considerable pellet and clear supernatant. The supernatant was carefully removed, the protein level (=non-encapsulated protein) was determined by reverse phase HPLC after diluting with phosphate buffered saline and 0.01% (v/v) Tween 80.

The pellet was solubilized with 300 µl of a 20% (w/v) Triton X-100 solution, followed by vigorous shaking. Surprisingly, the inventors found that the addition of Poly-L-Lysin e.g. 50 µl of a 2% (w/v) Poly-L-Lysin solution was necessary for dissociating the protein bound to the lipids by ionic interaction. After dilution with 550 µl 50% (v/v) acetonitril/0.1% (v/v) trifluoro acetic acid the protein concentration was determined by reverse phase HPLC.
Method B: Determinaton by Dialysis 1 ml of reconstituted liposomes was transferred into a hose of nitrocellulose ester membrane. The solution was subsequently dialyzed against 30 ml of 350 mM arginine/$H_3PO_4$ pH 7.5/0.1% (w/v) bovine serum albumin. The purification of the liposomal solution was completed after 4 hours of incubation at 4° C. and gentle shaking. The amount of non-encapsulated protein dialyzed into the acceptor medium was determined directly by reverse phase HPLC.
Method C: Determination by Centrifugation/ultra Filtration 125 µl of the rehydrated liposomal solution were centrifuged in a ultra filtration unit (Amicon Microcon Ultracel YM-100 units, Millipore, CAT.No.: 42413, 100,000 Da cut-off) at 13,200 rcf for 60 minutes. This step led to separation of the liposomes from the surrounding solution. In the filtrate the amount of the non encapsulated BMP-2 was determined by measuring concentration of BMP-2 by RP-HPLC using a standard curve and the volume of the permeate.

Example 6

Preparation of DRVs Using Various Lipids

Instead of using the phosphatidylcholine and cholesterol as components for the preparation of liposomes several other lipids were tested for total substitution or partial add-on for the lipid composition.
A. Fully Saturated Lipids 1 g of fully saturated soy lecithin (LIPOID SPC-3) was dissolved in 20 ml ethanol and a solution of 10% SUV could be obtained after preparation according to example 1A. 300 µl of the SUV solution were mixed with 250 µl CD-RAP solution (0.3 mg/ml in 420 mM Arg/$PO_4$ pH 7.5) and lyophilized in a glass vial resulting in a very stable lyo cake. After addition of 300 µl destilled water the rehydration of the lyo cake took place in a very slow manner not under 20 minutes, which failed the requirements for a fast injectable product.
B. Addition of Negatively Charged Lipids The liposomal formulation of CD-RAP in DRV was performed according to example 1A except the introduction of negatively charged lipids in the lipid composition of soy lecithin and cholesterol.
1. Addition of Cardiolipin Cardiolipin was added in amounts of 0 mg, 5 mg, 10 mg, 15 mg, 25 mg and 100 mg to 375 mg phosphatidylcholine (Lipoid S100), and 125 mg cholesterol and solved subsequent in 10 ml ethanol. The further proceeding e.g. preparation SUV, formulation, freeze drying was done according to example 1A. After rehydration of the lipid/protein cake with 0.3 ml destilled water and shaking multilamellar vesicles were obtained in the samples containing 0 mg-25 mg cardiolipin showing a rapid increase of viscosity. The sample containing 100 mg cardiolipin resulted in a gel-like solution with high viscosity with only very small vesicles (400 nm measured by photon correlation spectroscopy).

The diameter of the liposomes was determined by photon correlation spectroscopy resulting in an increase starting at an average diameter of 1500 nm to final 2500 nm with a cardiolipin addition of 25 mg.

2. Addition of Ascorbylpalmitate

Ascorbylpalmitate was added in amounts of 0 mg, 2.5 mg, 5 mg, 10 mg, 25 mg, 50 mg and 100 mg to 750 mg phosphatidylcholine (Lipoid S100), and 250 mg cholesterol and solved in 20 ml ethanol. The further proceeding e.g. preparation SUV, formulation, freeze drying was done according to example 1A. After rehydration of the lipid/protein cake with 0.3 ml destilled water and shaking multilamellar vesicles were obtained only in the samples containing 0 mg-50 mg ascorbylpalmitate showing a rapid increase of viscosity according to the addition of cardiolipin. The sample containing 100 mg ascorbylpalmitate resulted in a gel-like solution with a very high viscosity.

Figure 2:
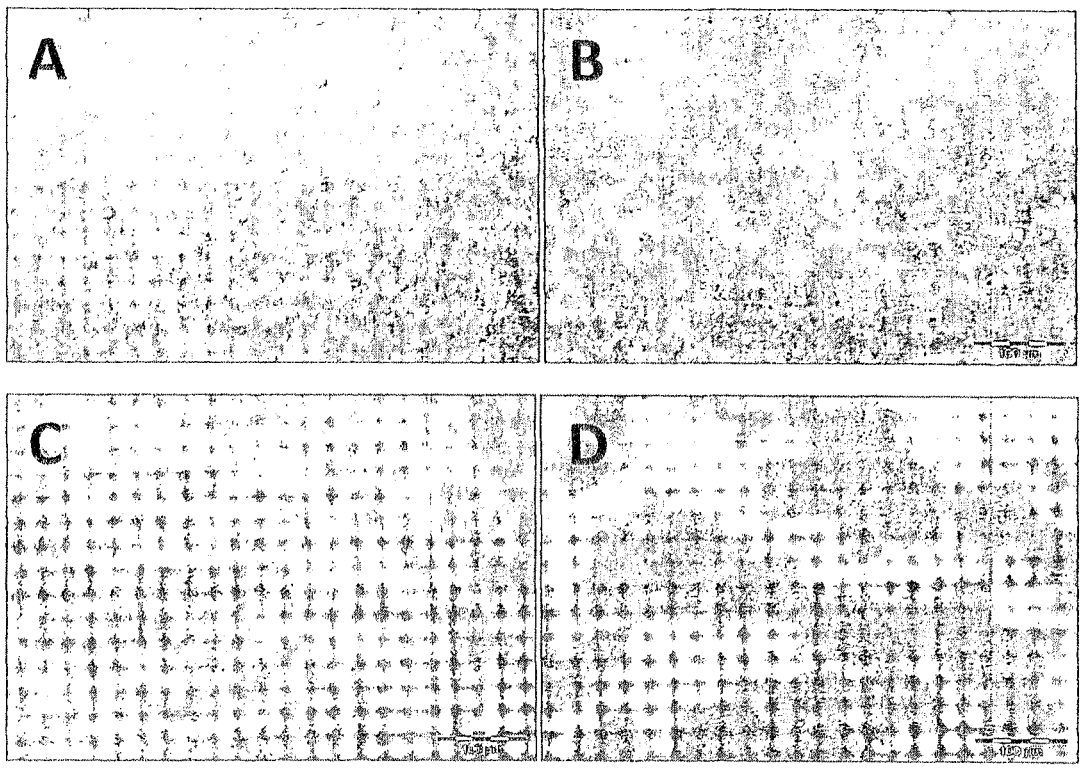
FIG. 2 illustrates the morphology of rehydrated liposomes analyzed by light microscopy in double polarized light.
Figure 3:
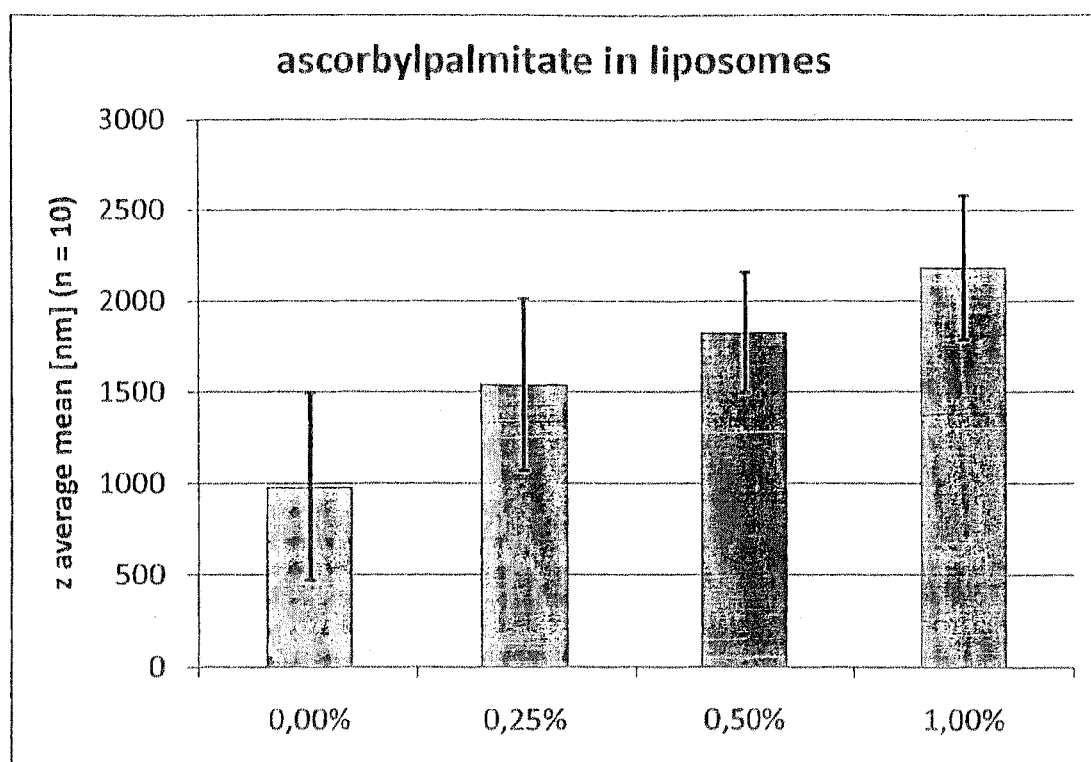
FIG. 3 shows the average size distribution of MLVs±standard deviation manufactured according to example 6B after reconstitution dependent of the amount of ascorbylpalmitate used.

However, surprisingly the multilamellar liposomes show a strong tendency to agglomeration with high amounts e.g. 1% or more of asorbylpalmitate (FIG. 2) and larger diameters (FIG. 3) with increasing amount of ascorbylpalmitate after rehydration in contrast to what is described in the literature (Liposomes $2^{nd}$ edition, A Practical Approach, edited by Vladimir P. Torchilin and Volkmar Weissig, Oxford University Press (2002), page 7) incorporated by reference herewith.

Example 7

Encapsulation of rhBMP-2 in Reconstituted DRVs

Freeze dried liposomes were manufactured according to example 1A using 750 mg phosphatidylcholine (Lipoid S100) and 250 mg cholesterol. 300 µl of SUVs were mixed with 250 µl rh-BMP-2 solution (0.50 mg/ml in 420 mM arginine/$H_3PO_4$ pH 7.5 and 5.0) and were subsequently lyophilized. Two different rh-BMP-2 preparations were used, *E. coli* derived rhBMP-2 (Ruppert, R. et al. (1996) Human bone morphogenetic protein 2 contains a heparin-binding site which modifies its biological activity. Eur. J Biochem. 237: 295-302) and CHO derived rhBMP-2 (InductOs, Wyeth Pharma GmbH). Rehydration with 300 µl led to an entrapment efficacy of more than 80% into MLV with a diameter of about 1.5 µm. The encapsulation efficacy was determined according Method C—centrifugation/ultra filtration. All measurements are done in duplicate. The results are shown in Table 2.

TABLE 2

Mass balance of liposomal encapsulation of rhBMP-2 in arginine/$H_3PO_4$ at various pH-values

| variant | not encapsulated | encapsulated |
|---|---|---|
| rhBMP-2, non glycosylated, pH 7.4 | 18% | 82% |
| rhBMP-2, non glycosylated, pH 5.0 | 17% | 83% |

Example 8

Rabbit Anterior Crucial Ligament Transection Model

To evaluate whether MIA/CD-RAP alleviates or prevents cartilage degradation in an animal model of osteoarthrithis a rabbit anterior cruciate ligament transection model was used. Under general anaesthesia and sterile conditions, the knee joint of rabbits were approached via a medial parapatellar incision (between the medial collateral ligament and patellar ligament). The patella was displaced laterally and the infrapatellar fat pad was mobilized and retracted to expose the entire anterior cruciate ligament. The incision was sutured in layers and an adhesive bandage was applied after suturing. The intraarticular injection was performed under fluoroscopy and sedation. The surgery and injection schedule was as follows: 6 animals were used per group (group 1: sham (ACL was not transected, group 2: lipoosomes, group 3: liposomes plus low dose MIA/CD-RAP, group 4: liposomes plus mid dose MIA/CD-RAP, group 5: liposomes plus high dose MIA/CD-RAP) n=30). The animals with the exception of the animals in the sham group were subjected to 5 injections. The injections were done every days. Animals were killed 10 days after the final injection and X-rays were obtained.

Subsequently, samples were fixed in 10% neutral buffered formaline, were decalcified in EDTA and embedded in paraffin. The cuts were stained with safranin O-fast green and hematoxylin and eosin and were histologically analyzed.

In this model multilamellar liposomes delivering CD-RAP decreased cartilage destruction and progression. The histological analysis demonstrated the efficacy of the injection of CD-RAP encapsulated in liposomes in the intrarticular space at mid dose and high dose of CD-RAP that reduced the development of OA ($p<0.05$). CD-RAP delivered in mid dose appeared to be most potent to prevent the development of OA as demonstrated by the intensity of the safranin O staining that was maintained in the mid dose group as compared to the sham group ($p<0.05$). The radiological analysis showed the prevention of the progression of OA in all treatment groups, CD-RAP low, mid and high dose groups ($p<0.05$).

Example 9

Annulus Fibrosus Puncture Model

In this example, an injection of CD-RAP is effective in partially restoring the disc height in a rabbit annular puncture model.

Disc degeneration can be induced in adolescent New Zealand White Rabbits by puncture of the annulus fibrosus into the disc using defined needle gauges (Singh, K. et al. (2005) Animal models for human disc degeneration. Spine J 5: 267S-279S). After provision of a local anaesthetic by injection of lidocain to the dorsal region of the disc lateral plain radiographs are obtained to determine preinjection baseline values for IVD heights. Subsequently the rabbits are placed into a lateral prone position and a posterolateral retroperitoneal approach is used to expose the lumbar IVDs. In each rabbit the AF will be punctured with a 18 G needle. After four weeks the animal receive an injection of buffered saline (in PBS) or vehicle liposomes as a control or protein solution of 2.5 mg/ml CD-RAP (in PBS) or liposomal encapsulated CD/RAP (2.5 mg/ml) into the nucleus pulposus and are followed for 12 weeks. Preclinical outcome is analyzed by magnetic resonance imaging (MRI) scans of the lumbar spine, IVD height monitored by radiological observation measured with a custom program using Imaging software and the % DHI (postoperative DHI/preoperative DIH×100) is calculated. For histological analysis of the IVDs, sections are stained with Hematoxylin Eosin and Safranin O. Differences among groups are assessed for statistical significance by using a one-way analysis of variance (ANOVA).

Each rabbit will have one disc treated with CD-RAP in saline solution, the other with saline solution or liposomes or liposomal encapsulated CD-RAP.

The invention claimed is:

1. A dried pharmaceutical composition comprising freeze dried active agent comprising vesicles comprising
   a) at least one lipid, wherein the lipid comprises phosphatidylcholine
   b) at least one active agent, and
   c) a fusion promoting agent, wherein the fusion promoting agent is an alkaline amino acid selected from arginine, histidine, lysine or citrulline
   wherein rehydration of the dried pharmaceutical composition with an aqueous solution results in the formation of multilamellar liposomes having an average liposomal diameter of more than 1 μm, which liposomes encapsulate the active agent,
   wherein no protective sugar, sugar alcohol or glycoside is present,
   wherein the at least one active agent is a protein, wherein the protein comprises the mature sequence of CD-RAP (SEQ ID NO:1) and functional fragments or variants thereof.

2. The dried pharmaceutical composition according to claim 1, further comprising an inorganic or organic anion.

3. The dried pharmaceutical composition according to claim 2, wherein the inorganic or organic anion is succinate, fumarate, citrate, malate, phosphate, acetate, or chloride.

4. The composition of claim 1, wherein the lipid further comprises a second neutral lipid.

5. The composition of claim 4, wherein the second lipid comprises cholesterol (Chol).

6. A pharmaceutical freeze dried composition obtainable by a process comprising the steps of
   a) hydratization of a lipid, lipid mixture or lipid film comprising phosphatidylcholine in the absence of an organic solvent,
   b) generation of small unilamellar vesicles preferably with an average diameter between 50 and 200 nm,
   c) addition of aqueous solution of an active agent, said active agent comprises the mature sequence of CD-RAP (SEQ ID NO:1) and functional fragments or variants
   d) after, before or together with step c), addition of a fusion promoting agent, wherein the fusion promoting agent is an alkaline amino acid selected from arginine, histidine, lysine or citrulline, and optionally of an inorganic or organic anion, and e) dehydration of said lipid dispersion without the addition of a protective sugar, sugar alcohol or glycoside.

7. A pharmaceutical composition obtainable by a process comprising the steps of
   a) hydratization of a lipid, lipid mixture or lipid film comprising phosphatidylcholine in the absence of an organic solvent,
   b) generation of small unilamellar vesicles preferably with an average diameter between 50 and 200 nm,
   c) addition of aqueous solution of an active agent, said active agent comprises the mature sequence of CD-RAP (SEQ ID NO:1) and functional fragments or variants thereof
   d) after, before or together with step c), addition of a fusion promoting agent, wherein the fusion promoting agent is an alkaline amino acid selected from arginine, histidine, lysine or citrulline, and optionally of an inorganic or organic anion,
   e) dehydration of said lipid dispersion without the addition of a protective sugar, sugar alcohol or glycoside, and
   f) rehydration with an aqueous solution and formation of multilamellar vesicles having an average liposomal diameter of more than 1 μm encapsulating the active agent, wherein a step of sterile filtration is performed after step b) and/or c).

* * * * *